United States Patent

Matsuzawa et al.

[11] Patent Number: 4,875,930
[45] Date of Patent: Oct. 24, 1989

[54] CYCLOHEXANE DERIVATIVES HAVING PLANT GROWTH REGULATING ACTIVITIES AND APPLICATIONS THEREOF

[76] Inventors: Masafumi Matsuzawa; Hiroshi Hokari; Shoji Kusano, all of 132, Ojima, Fukude-cho, Iwata-gun, Shizuoka-ken; Takeshige Miyazawa; Yasufumi Toyokawa, both of 1809, Kamo, Kikugawa-cho, Ogasa-gun, Shizuoka-ken, all of Japan

[21] Appl. No.: 186,663

[22] Filed: Apr. 26, 1988

Related U.S. Application Data

[63] Continuation of Ser. No. 854,879, Apr. 21, 1986, abandoned.

[30] Foreign Application Priority Data

Apr. 26, 1985 [JP] Japan ................................. 60-90675
Mar. 18, 1986 [JP] Japan ................................. 61-59986

[51] Int. Cl.$^4$ ..................... A01N 37/00; C07C 69/74
[52] U.S. Cl. ........................... 71/106; 71/121; 71/124; 560/48; 560/125; 560/126; 260/396 N
[58] Field of Search ................ 562/507, 457; 564/300, 564/256, 339, 342; 560/125, 126, 179, 46, 39, 40, 45; 556/182, 184; 71/121, 106, 124; 260/502.56, 396 N

[56] References Cited

U.S. PATENT DOCUMENTS

| | | | |
|---|---|---|---|
| 3,933,472 | 1/1976 | Buckman et al. | 71/121 |
| 3,950,420 | 4/1976 | Sawaki et al. | 564/300 |
| 3,973,944 | 8/1976 | Erdmann et al. | 71/121 |
| 4,618,360 | 10/1986 | Brunner | 562/507 |

FOREIGN PATENT DOCUMENTS 54-16454  2/1979  Japan ................................. 564/300

Primary Examiner—Richard L. Raymond
Assistant Examiner—Raymond Covington
Attorney, Agent, or Firm—Larson and Taylor

[57] ABSTRACT

As new compound is provided a cyclohexane derivative of the formula

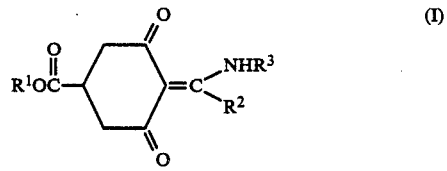

(I)

wherein $R^1$ is a hydrogen or a lower alkyl; $R^2$ is a lower alkyl; $R^3$ is a hydrogen, an alkyl, an alkenyl, a hydroxyalkyl, a cycloalkyl, a morpholino, an aminoalkyl, an N-alkylaminoalkyl, an N,N-di-alkylaminoalkyl, an alkoxycarbonylalkyl, a group of the formula —(CH$_2$)$_l$—R$^4$ where R$^4$ is a lower alkoxy, a lower alkylthio, a benzylthio, an anilino, a morpholino, a piperazino, a piperidino or a lower alkyl-substituted piperidino and l is 2 or 3, a group of the formula

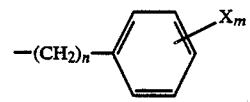

where X is a halogen, a lower alkyl, a lower alkoxy, a phenoxy or an alkoxycarbonylalkyloxy, m is zero or 1 and n is an integer of zero to 2, inclusive, a group of the formula —CH$_2$—R$^5$ where R$^5$ is a furyl, a thenyl or a pyridyl, or a group of the formula

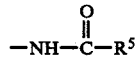

where $R^5$ is as defined above; or a salt of said cyclohexane derivative.

This cyclohexane derivative exhibits useful plant growth regulating effects on crop-plants and also non-crop-plant such as lawn.

19 Claims, No Drawings

CYCLOHEXANE DERIVATIVES HAVING PLANT GROWTH REGULATING ACTIVITIES AND APPLICATIONS THEREOF

This application is a continuation of application Ser. No. 854,879 filed 04/21/86 now abandoned.

FIELD OF THE INVENTION

This invention relates to novel cyclohexane derivatives, more specifically 4-(1-amino- or substituted amino-lower alkylidene)-3,5-dioxocyclohexane carboxylic acids and their lower alkyl esters and their salts with primary amines. These cyclohexane derivatives possess high plant growth regulating activities. Thus, this invention also relates to a plant growth regulating agent comprising such novel cyclohexane derivative as active ingredient and further to a method of regulating the growth of plant using such agent.

BACKGROUND OF THE INVENTION

A variety of chemical compounds have been proposed and actually used for the purpose of regulating the growth of plants with a chemical substance, that is for the purpose of so-called "chemical control" of the growth of plants. Thus, maleic hydrazide (MH), N,N-dimethylaminosuccinamide (known as Daminozide) and 2-chloroethyl trimethyl ammonium chloride (known as Chlormequat) have been used for retardation of the growth of plants, for control of emergence of sideshooting or for prevention of the lodging of plants. These known compounds, however, have various drawbacks such that their applications are restricted in respect of the locus, nature of plants and time which can effectively be treated therewith, that their plant growth regulating effects are insufficient or unstable, that they are phytotoxic, and/or that they are too expensive. Further, in the application of a plant growth regulating agent to lawns, it is in general desirable to use such kind of a regulating agent as to exhibit a growth retarding effect with little or minimum fluctuation thereof over a wide variety of the kinds of lawns for making the mowing of lawns easier because a plurality of species of lawns are often blended for seeding in order to adapt various environmental stresses occurred such as plant diseases and harmful insects, wheather and soil conditions, etc. Most of known types of plant growth regulators do not meet such applications.

During our extensive investigations being made with the intention of providing new plant growth regulators which have little or no such drawbacks of the known regulators as above-mentioned, we have already found that a class of cyclohexane derivatives which we have first synthesized exhibit significant plant growth regulating activities without substantially suffering from the above-said drawbacks. The cyclohexane derivatives are those having the general formula:

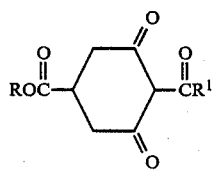

wherein R represents a hydrogen atom or an alkyl, alkylthioalkyl, or unsubstituted or substituted phenyl group; and $R^1$ represents an alkyl, unsubstituted or substituted benzyl, phenethyl, phenoxymethyl, 2-thienylmethyl, alkoxymethyl or alkylthiomethyl group, and their salts (refer to Japanese patent application Kokai Nos. 164543/83 and 196840/84 and U.S. Pat. No. 4,560,403).

Another class of cyclohexane derivatives is disclosed in European patent application Prepublication No. 0126713 (Application Nos. 84810233.1 filed by Ciba-Geigy AG) and corresponding Japanese patent application Kokai No. 231045/84), which is represented by the general formula:

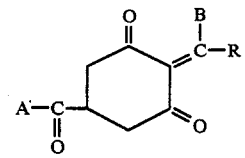

wherein A is $-OR_2$ or $-NR_3R_4$; B is $-OH$, $-NHOR_1$ or a metal or ammonium salt thereof; R is $C_1-C_6$ alkyl or $C_3-C_6$ cycloalkyl, unsubstituted or substituted by halogen, $C_1-C_4$ alkoxy or $C_1-C_4$ alkylthio; $R_1$ is $C_1-C_6$ alkyl, $C_1-C_6$ haloalkyl, $C_3-C_6$ alkenyl, $C_3-C_6$ haloalkenyl or $C_3-C_6$ alkynyl; $R_2$, $R_3$ and $R_4$ each are hydrogen, $C_1-C_6$ alkyl, $C_1-C_6$ haloalkyl, $C_2-C_{10}$ alkoxyalkyl, $C_2-C_{10}$ alkylthioalkyl, $C_3-C_6$ alkenyl, unsubstituted or substituted by halogen, $C_1-C_4$ alkoxy or $C_1-C_4$ alkylthio, $C_3-C_6$ alkynyl, phenyl or $C_1-C_6$ aralkyl where the phenyl nucleous may be unsubstituted or substituted by halogen, $C_1-C_4$ alkyl, $C_1-C_4$ alkoxy, $C_1-C_4$ haloalkyl, nitro or cyano; or $R_3$ and $R_4$ may form together with the nitrogen atom to which they are bonded a 5- or 6-membered heterocyclic group which may further contain oxygen or sulfur hetero atom.

As far as we, the present inventors, have synthesized and tested two particular compounds amongst many examples of the compound of the above formula according to the European patent application prepublication No. 0126713, such cyclohexane derivatives of the above formula where A is $-OC_2H_5$, B is $-NHOC_2H_5$ and R is $-C_3H_7$-n; and where A is $-OC_2H_5$, B is $-N-HOCH_2CH=CH_2$ and R is $-C_3H_7$-n do not necessarily have satisfactorily high activities on applications for the plant growth regulation.

We have further continued our investigations on the preparation and application as plant growth regulators of a wide variety of new cyclohexane derivatives and their salts, and have now found a new class of cyclohexane derivatives to be excellent plant growth regulators particularly in that their plant growth retarding activities are even less variant over various kinds of lawns than those of the known cyclohexane derivatives we propose and in that they have little or no such drawbacks of the conventional plant growth regulators as above-mentioned.

SUMMARY OF THE INVENTION

According to a first aspect of this invention, therefore, there are provided a cyclohexane derivative having general formula (I)

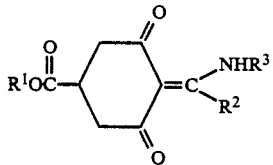

(I)

wherein $R^1$ is a hydrogen atom or a lower alkyl group; $R^2$ is a lower alkyl group; $R^3$ is a hydrogen atom, an alkyl group, an alkenyl group, a hydroxyalkyl group, a cycloalkyl group, a morpholino group, an aminoalkyl group, an N-alkylaminoalkyl group, an N,N-dialkylaminoalkyl group, an alkoxycarbonylalkyl group, a group of the formula —$(CH_2)_l$—$R^4$ where $R^4$ is a lower alkoxy group, a lower alkylthio group, a benzythio group, an anilino group, a morpholino group, a piperazino group, a piperidino group or a lower alkyl-substituted piperidino group and l is 2 or 3, a group of the formula

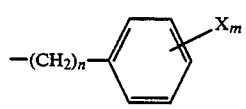

where X is a halogen atom, a lower alkyl group, a lower alkoxy group, a phenoxy group or an alkoxycarbonylalkyloxy group, m is zero or 1 and n is an integer of zero to 2, inclusive, a group of the formula —$CH_2$—$S^5$ where $R^5$ is a furyl group, a thenyl group or a pyridyl group, or a group of the formula

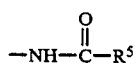

where $R^5$ is as defined above; and a salt of said cyclohexane derivative.

DETAILED DESCRIPTION OF THE INVENTION

The salts of the cyclohexane derivatives of general formula (I) are typically amine salts, particularly those represented by the formula:

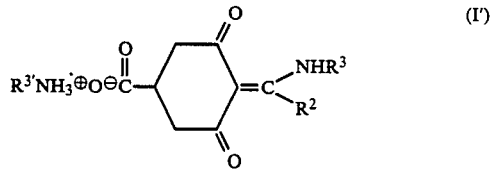

(I')

wherein $R^2$ and $R^3$ have the same meanings as defined above and $R^{3'}$ has the same meaning as $R^3$ except excluding a group of the formula

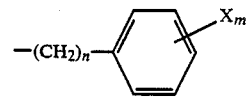

where n=0.

The novel cyclohexane derivatives of formula (I) according to this invention may take the tautomeric structures as undermentioned and all these structures are within the scope of the compounds of this invention.

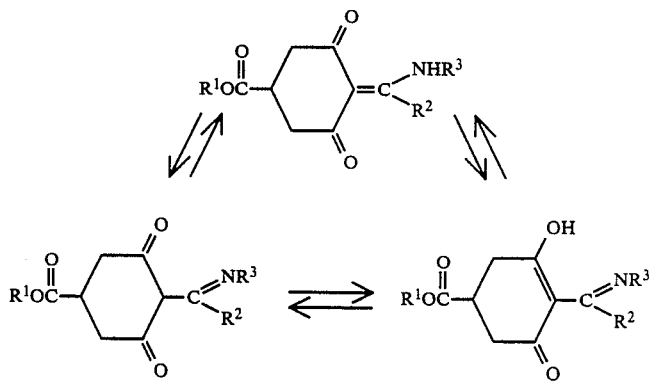

Typical examples of the cyclohexane derivatives of general formula (I) or their amine salts are listed in Table 1 below, where some physical properties of each compound are also shown. In Table 1, the compounds with an asterisk are in the form of amine salts of $R^{3'}NH_3$ in place of $R^1$ in formula (I) and the compound with two asterisks is an acid addition salt at $R^3$ in formula (I).

TABLE 1

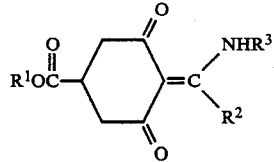
(I)

| Compound No. | $R^1$ or $R^{3'}NH_3$ | $R^2$ | $R^3$ | Melting point or Refractive index |
|---|---|---|---|---|
| 1 | $CH_3$ | $CH_3$ | $CH_3$ | 91–93° C. |
| 2 | " | " | $C_2H_5$ | 76.5–78.5° C. |
| 3 | $C_2H_5$ | $C_2H_5$ | " | $n_D^{20}$ 1.5348 |
| 4 | " | $n\text{-}C_3H_7$ | " | $n_D^{20}$ 1.5275 |
| 5 | $CH_3$ | " | $n\text{-}C_3H_7$ | $n_D^{20}$ 1.5288 |
| 6 | " | $C_2H_5$ | " | 55–57° C. |
| 7 | $C_2H_5$ | " | $i\text{-}C_3H_7$ | $n_D^{20}$ 1.5246 |
| 8 | $i\text{-}C_3H_7$ | " | " | $n_D^{20}$ 1.5155 |
| 9 | $C_2H_5$ | " | $sec\text{-}C_4H_9$ | $n_D^{20}$ 1.5249 |
| 10 | " | " | $-C_2H_4NHC_2H_5$ | $n_D^{20}$ 1.5269 |
| 11 | " | " | $-C_3H_6NHCH_3$ | $n_D^{20}$ 1.5368 |
| 12 | " | " | $-\underset{\underset{CH_3}{\mid}}{CH}-C_3H_6N(C_2H_5)_2$ | $n_D^{20}$ 1.5169 |
| 13 | " | " | $-C_3H_6N(C_4H_9\text{-}n)_2$ | $n_D^{20}$ 1.5133 |
| 14 | $C_2H_5$ | $C_2H_5$ | $-C_2H_4OH$ | $n_D^{20}$ 1.5474 |
| 15 | " | " | $-(CH_2)_5OH$ | $n_D^{20}$ 1.5379 |
| 16 | " | " | $-CH_2C_6H_5$ | $n_D^{20}$ 1.5730 |
| 17 | " | " | $-CH_2\text{-}(2\text{-}Cl\text{-}C_6H_4)$ | 56–58° C. |
| 18 | " | " | $-CH_2\text{-}(4\text{-}Cl\text{-}C_6H_4)$ | $n_D^{20}$ 1.5801 |
| 19 | " | " | $-CH_2\text{-}(4\text{-}CH_3\text{-}C_6H_4)$ | 61–62° C. |
| 20 | " | " | $-C_6H_5$ | 108–110° C. |
| 21 | $CH_3$ | " | " | 146–147° C. |
| 22 | " | $CH_3$ | " | 118–119° C. |
| 23 | $C_2H_5$ | " | " | 122–123° C. |
| 24 | $CH_3$ | $n\text{-}C_3H_7$ | " | 83–84° C. |
| 25 | " | $C_2H_5$ | $2\text{-}CH_3\text{-}C_6H_4$ | 83–84° C. |
| 26 | $C_2H_5$ | " | " | $n_D^{20}$ 1.5738 |

TABLE 1-continued $$R^1OC(=O)\text{-cyclohexane-1,3-dione with }=C(R^2)(NHR^3)\text{ substituent}\quad (I)$$

| Compound No. | $R^1$ or $R^{3'}NH_3$ | $R^2$ | $R^3$ | Melting point or Refractive index |
|---|---|---|---|---|
| 27 | " | " | 2-Cl-C₆H₄- | $n_D^{20}$ 1.5760 |
| 28 | " | " | 4-OC₂H₅-C₆H₄- | 79–80° C. |
| 29 | C₂H₅ | C₂H₅ | 3-OC₃H₇-i-C₆H₄- | 91–93° C. |
| 30 | " | " | 4-phenoxyphenyl | 92–93° C. |
| 31 | " | " | —CH₂COC₂H₅ | 90–92° C. |
| 32 | H | " | C₆H₅ | 205–207° C. |
| 33* | HOCH₂CH₂NH₃ | " | —CH₂CH₂OH | 118–119° C. |
| 34 | C₂H₅ | n-C₃H₇ | —C₂H₄OH | $n_D^{20}$ 1.5258 |
| 35 | " | " | 3-OC₃H₇-i-C₆H₄- | $n_D^{20}$ 1.5360 |
| 36 | " | C₂H₅ | CH₃ | $n_D^{20}$ 1.5366 |
| 37 | " | " | n-C₄H₉ | $n_D^{20}$ 1.5275 |
| 38 | CH₃ | " | —C₂H₄OH | $n_D^{20}$ 1.5570 |
| 39 | C₂H₅ | " | —C₃H₆OH | $n_D^{20}$ 1.5361 |
| 40 | " | CH₃ | —C₂H₄OH | $n_D^{20}$ 1.5325 |
| 41 | " | C₂H₅ | —C₃H₆N(CH₃)₂ | $n_D^{20}$ 1.5291 |
| 42 | " | " | 4-Cl-C₆H₄- | 81–82° C. |
| 43 | " | " | 4-CH₃-C₆H₄- | 93.5–95.5° C. |

TABLE 1-continued (I)

R¹OC(=O)—[cyclohexane-1,3-dione with =C(R²)(NHR³) at position 2]

| Compound No. | R¹ or R³'NH₃ | R² | R³ | Melting point or Refractive index |
|---|---|---|---|---|
| 44 | " | " | –C₆H₄–OCH₃ (para) | 76–78° C. |
| 45 | C₂H₅ | C₂H₅ | –C₆H₄–C₃H₇-i (para) | 81–82° C. |
| 46 | " | " | –CH(C₂H₅)CH₂OH | $n_D^{20}$ 1.5365 |
| 47 | CH₃ | " | i-C₃H₇ | $n_D^{20}$ 1.5338 |
| 48 | C₂H₅ | " | –C₆H₄–OCH₃ (ortho) | $n_D^{20}$ 1.5790 |
| 49 | " | " | –C₆H₄–OCH₃ (meta) | 49–51° C. |
| 50 | " | " | –CH₂–C₆H₄–F (para) | $n_D^{20}$ 1.5648 |
| 51 | " | " | –O–C₆H₄–OC₂H₅ (ortho) | 99–101° C. |
| 52 | CH₃ | n-C₃H₇ | CH₃ | $n_D^{20}$ 1.5385 |
| 53 | " | " | C₂H₅ | $n_D^{20}$ 1.5278 |
| 54 | " | " | i-C₃H₇ | $n_D^{20}$ 1.5225 |
| 55 | " | " | 2,6-dimethylphenyl | $n_D^{20}$ 1.5592 |
| 56 | " | C₂H₅ | CH₃ | 71–72° C. |
| 57 | " | " | C₂H₅ | $n_D^{20}$ 1.5457 |
| 58 | C₂H₅ | " | n-C₃H₇ | 48–49° C. |
| 59 | " | n-C₃H₇ | CH₃ | $n_D^{20}$ 1.5373 |
| 60 | C₂H₅ | n-C₃H₇ | n-C₃H₇ | $n_D^{20}$ 1.5273 |
| 61 | " | " | i-C₃H₇ | $n_D^{20}$ 1.5261 |

TABLE 1-continued (I)

$$R^1OC(=O)-\text{cyclohexanedione}=C(R^2)-NHR^3$$

| Compound No. | R¹ or R³'NH₃ | R² | R³ | Melting point or Refractive index |
|---|---|---|---|---|
| 62 | " | " | phenyl | 82–83° C. |
| 63 | " | " | 2-methylphenyl | $n_D^{20}$ 1.5692 |
| 64 | " | CH₃ | CH₃ | 74–75° C. |
| 65 | " | " | C₂H₅ | 49–50° C. |
| 66 | " | " | n-C₃H₇ | 58–59° C. |
| 67 | " | " | i-C₃H₇ | 55–56° C. |
| 68 | " | " | 2-methylphenyl | 95–96° C. |
| 69 | CH₃ | " | n-C₃H₇ | 56–57.5° C. |
| 70 | " | " | i-C₃H₇ | 41–42° C. |
| 71 | " | " | 2-methylphenyl | 138–140° C. |
| 72 | C₂H₅ | C₂H₅ | i-C₄H₉ | $n_D^{20}$ 1.5252 |
| 73* | n-C₃H₇NH₃ | " | n-C₃H₇ | $n_D^{20}$ 1.5322 |
| 74* | HOCHCH₂NH₃ \| CH₃ | " | —CH₂CHOH \| CH₃ | 140–143° C. |
| 75 | C₂H₅ | " | H | 69–71° C. |
| 76 | C₂H₅ | C₂H₅ | —C₂H₄OCH₃ | $n_D^{20}$ 1.5332 |
| 77 | " | " | —C₃H₆OCH₃ | $n_D^{20}$ 1.5266 |
| 78 | " | " | cyclohexyl-H | $n_D^{20}$ 1.5413 |
| 79 | " | " | cyclopentyl-H | $n_D^{20}$ 1.5440 |
| 80 | " | " | —C₂H₄-phenyl | $n_D^{20}$ 1.5655 |

TABLE 1-continued
$$\text{(I)}$$
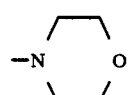
| Compound No. | R¹ or R³′NH₃ | R² | R³ | Melting point or Refractive index |
|---|---|---|---|---|
| 81 | " | " | 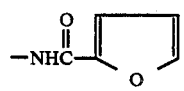 | 67–68° C. |
| 82 | " | " | 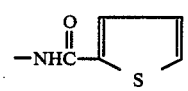 | 103–105° C. |
| 83 | " | " | 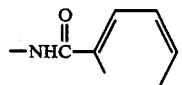 | 97–99° C. |
| 84 | " | " | 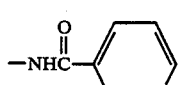 | 154–156° C. |
| 85 | " | " | 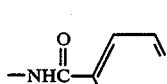 | 117–119° C. |
| 86 | " | " | 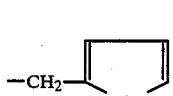 | 165–167° C. |
| 87 | " | " | 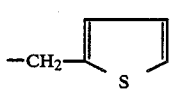 | $n_D^{20}$ 1.5513 |
| 88 | " | " | 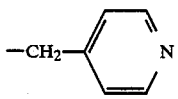 | $n_D^{20}$ 1.5832 |
| 89 | " | " | 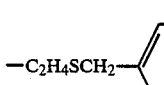 | $n_D^{20}$ 1.5702 |
| 90 | $C_2H_5$ | $C_2H_5$ | $-C_2H_4SCH_3$ | $n_D^{20}$ 1.5600 |
| 91 | " | " | $-C_2H_4SCH_2-\text{C}_6\text{H}_5$ | $n_D^{20}$ 1.5835 |
| 92 | " | " | 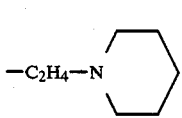 | $n_D^{20}$ 1.5338 |

TABLE 1-continued (I)

$$R^1OC(=O)\text{-cyclohexane-1,3-dione-2-}C(=C)(R^2)(NHR^3)$$

| Compound No. | $R^1$ or $R^{3'}NH_3$ | $R^2$ | $R^3$ | Melting point or Refractive index |
|---|---|---|---|---|
| 93 | " | " | —C₃H₆—N(2-methylpiperidinyl) | $n_D^{20}$ 1.5318 |
| 94 | " | " | —C₃H₆—N(morpholinyl) | $n_D^{20}$ 1.5333 |
| 95** | " | " | —C₂H₄NH₂C₂H₅·COOH (with COO⁻) | 182–184° C. |
| 96 | " | " | —CH₂CH=CH₂ | $n_D^{20}$ 1.5428 |
| 97 | " | " | —CH₂—C(CH₃)₂—NH₂ | 86–88° C. |
| 98 | " | " | —C₆H₄—OCH(CH₃)COC₂H₅ | 75–77° C. |
| 99 | " | " | —C₂H₄—NH—C₆H₅ | $n_D^{20}$ 1.5815 |
| 100 | " | " | —C₂H₄—N(piperazinyl)NH | $n_D^{20}$ 1.5506 |
| 101* | (CH₃)₂N(CH₂)₃NH₃ | " | —(CH₂)₃N(CH₃)₂ | 128–130° C. |
| 102* | CH₃OC(=O)CH₂NH₃ | " | —CH₂COCH₃ | 213–215° C. |
| 103* | O(morpholinyl)N—NH₃ | C₂H₅ | —N(morpholinyl)O | 128–130° C. |
| 104* | i-C₃H₇NH₃ | " | —C₃H₇—i | 120–128° C. |
| 105* | n-C₄H₉NH₃ | " | —C₄H₉—n | 117–121° C. |
| 106* | n-C₄H₉—CH(C₂H₅)CH₂NH₃ | " | —CH₂CH(C₂H₅)—C₄H₉—n | 53–56° C. |
| 107* | CH₃O(CH₂)₃NH₃ | " | —(CH₂)₃OCH₃ | 63–65° C. |
| 108* | i-C₃H₇O(CH₂)₃NH₃ | " | —(CH₂)₃OC₃H₇—i | 67.5–70.5° C. |

Amongst the particular compounds given in Table 1, the following compounds are preferred in this invention: 4-[1-(2-hydroxyethylamino)propylidene]-3,5-dioxocyclohexane-carboxylic acid and · 2-hydroxyethylamine salt thereof (Compound No. 33); ethyl 4-(1-phenylaminopropylidene)-3,5-dioxocyclohexane-carboxylate (Compound No. 20); ethyl 4-[1-(3-hydroxypropylamino)propylidene]-3,5-dioxocyclohexane-carboxylate (Compound No. 39); 4-[1-(2-hydroxypropylamino)propylidene]-3,5-dioxocyclohexane-carboxylic acid; 4-[1-(2-hydroxypropylamino)-propylidene]-3,5-dioxocyclohexane-carboxylic acid 2-hydroxypropylamine salt (Compound No. 74); ethyl 4-[1-(2-methoxyethylamino)propylidene]-3,5-dioxocyclohexane-carboxylate (Compound No. 76); ethyl 4-(1-(3-methoxypropylamino)propylidene]-3,5-dioxocyclohexane-carboxylate (Compound No. 77); and ethyl 4-[1-(2-methylthio-ethylamino)propylidene]-3,5-dioxocyclohexane-carboxylate (Compound No. 90).

The compounds of general formula (I) can be prepared, for example, according to the following reaction equation:

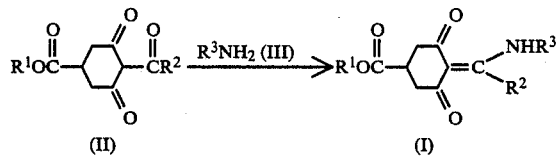

wherein $R^1$, $R^2$ and $R^3$ have the same meanings as defined above. Usually, compounds (II) and (III) are reacted in an equimolar proportion, but in cases where $R^1$ is hydrogen and $R^3$ is as defined above except $R^3$ being

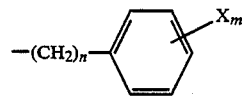

where X and m have the same meanings as defined above and n=0, two moles or more, preferably two moles, of compound (III) are reacted with one mole of compound (II) whereby to form a corresponding amine salt of compound (I), that is a compound of formula (I′) above.

The reaction between compounds (II) and (III) may be conducted in the presence or absence of a solvent at a temperature between room temperature and the boiling temperature of the solvent for about 0.1 to 10 hours. Exemplary of the usable solvents are alcohols such as methanol and ethanol; non-polar solvents such as benzene, toluene and xylene; acetic acid esters such as methyl acetate and ethyl acetate; and halogenated hydrocarbons such as dichloromethane and chloroform.

According to a first particular embodiment of the first aspect of this invention, there is provided a compound of general formula (I) where $R^1$ is a hydrogen atom or a lower alkyl group; $R^2$ is a lower alkyl group; and $R^3$ is a lower alkyl group, a hydroxyalkyl group, an N-alkylaminoalkyl group, an N,N,-dialkylaminoalkyl group, an alkoxycarbonylalkyl group or a group of the formula

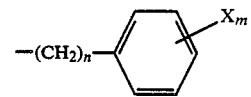

where X is a halogen atom, a lower alkyl group, a lower alkoxy group or a phenoxy group; m is zero or 1; and n is zero or 1; or an amine-addition salt of said compound.

The compound of this first embodiment includes the compounds of the following types:

(1) A compound of formula (I) where $R^1$ is a hydrogen atom or a lower alkyl group; $R^2$ is a lower alkyl group; and $R^3$ is a lower alkyl group; and an amine-addition salt of said compound.

(2) A compound of formula (I) where $R^1$ is a hydrogen atom or a lower alkyl group; $R^2$ is a lower alkyl group; and $R^3$ is a hydroxyalkyl group; and an amine-addition salt of said compound.

(3) A compound of formula (I) where $R^1$ is a hydrogen atom or a lower alkyl group; $R^2$ is a lower alkyl group; and $R^3$ is an N-alkylaminoalkyl group or an N,N-dialkylaminoalkyl group; and an amine-addition salt of said compound.

(4) A compound of formula (I) where $R^1$ is a lower alkyl group; $R^2$ is a lower alkyl group; and $R^3$ is an alkoxycarbonylalkyl group; and an amine-addition salt of said compound.

(5) A compound of formula (I) where $R^1$ is a hydrogen atom or a lower alkyl group; $R^2$ is a lower alkyl group; and $R^3$ is a phenyl group optionally bearing a halogen atom, an alkyl group, an alkoxy group or a phenoxy group as the substituent on the phenyl group.

The compounds of types (1), (2), (3) and (4) above may be in the form of an amine-addition salt of the compound of formula (I) where $R^1$ is a hydrogen atom, with an amine of the formula $R^{3'}$—$NH_2$ wherein $R^{3'}$ has the same meaning as $R^3$ above except excluding a group of the formula

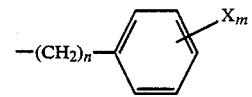

where n=0, preferably $R^{3'}$ is a hydroxy(lower)alkyl group, said amine being added to the carboxyl group of the compound of formula (I) where $R^1$ is a hydrogen atom.

According to a second particular embodiment of the first aspect of this invention, there is provided a compound of general formula (I) where $R^1$ is a hydrogen atom or a lower alkyl group; $R^2$ is a lower alkyl group; and $R^3$ is a hydrogen atom, an alkenyl group, a cycloalkyl group, a morpholino group, an aminoalkyl group, a group of the formula —$(CH_2)_l$—$R^4$ where $R^4$ is a lower alkoxy group, a lower alkylthio group, a benzylthio group, an anilino group, a morpholino group, a piperazino group, a piperidino group or a lower alkyl-substituted piperidino group and l is an integer of 2 or 3, a group of the formula

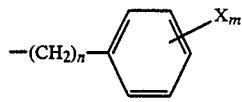

where X is an alkoxycarbonylalkyloxy group, m is zero or 1 and n is an integer or zero to 2, a group of the formula —CH$_2$R$^5$ where R$^5$ is a furyl group, a thenyl group or a pyridyl group or a group of the formula

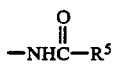

where R$^5$ is a furyl group, a thenyl group or a pyridyl group; or an amine-addition salt of said compound.

The compound of this second embodiment includes the compounds of the following types:

(6) A compound of formula (I) where R$^1$ is a hydrogen atom or a lower alkyl group; R$^2$ is a lower alkyl group; and R$^3$ is a group of the formula

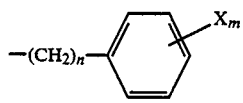

where X is a halogen atom, an alkyl group, an alkoxy group or a phenoxy group, m is zero or 1 and n is 1 or 2; and an amine-addition salt of said compound.

(7) A compound of formula (I) where R$^1$ is a hydrogen atom or a lower alkyl group; R$^2$ is a lower alkyl group; and R$^3$ is a group of the formula —(CH$_2$)$_l$—R$^4$ where R$^4$ is an alkoxy group and l is 2 or 3; and an amine-addition salt of said compound.

(8) A compound of formula (I) where R$^1$ is a hydrogen atom or a lower alkyl group; R$^2$ is a lower alkyl group; and R$^3$ is a group of the formula —(CH$_2$)$_l$—R$^4$ where R$^4$ is an alkylthio group or a benzylthio group and l is 2 or 3; and an amine-addition salt of said compound.

(9) A compound of formula (I) where R$^1$ is a hydrogen atom or a lower alkyl group; R$^2$ is a lower alkyl group; and R$^3$ is a group of the formula —(CH$_2$)$_l$—R$^4$ where R$^4$ is an anilino group, a morpholino groups, a piperazino group, a piperidino group or an alkyl-substituted piperidino group and l is 2 or 3; and an amine-additional salt of said compound.

(10) A compound of formula (I) where R$^1$ is a hydrogen atom or a lower alkyl group; R$^2$ is a lower alkyl group; and R$^3$ is a group of the formula —CH$_2$—R$^5$ where R$^5$ is a furyl group, a thenyl group or a pyridyl group; and an amine-addition salt of said compound.

(11) A compound of formula (I) where R$^1$ is a hydrogen atom or a lower alkyl group; R$^2$ is a lower alkyl group; and R$^3$ is a group of the formula

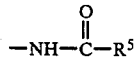

where R$^5$ is a furyl group, a thenyl group or a pyridyl group; and an amine-addition salt of said compound.

The compounds of types (6) to (11) above may be in the form of an amine-addition salt of the compound of formula (I) where R$^1$ is a hydrogen atom, with an amine of the formula R$^{3'}$—NH$_2$ where R$^{3'}$ is a hydroxy(lower)alkyl group, a (lower)alkyl group, a di-(lower)alkylamino(lower) alkyl group, a (lower)alkoxycarbonyl(lower)alkyl group, a morpholino group, or a (lower)alkoxy(lower)alkyl group, said amine being added to the carboxyl group of the compound of formula (I) where R$^1$ is a hydrogen atom.

The term "lower alkyl" group as given above means an alkyl containing 1 to 6 carbon atoms and especially 1 to 4 carbon atoms. The term "lower alkoxy" group means an alkoxy containing 1 to 6 carbon atoms and especially 1 to 4 carbon atoms. The terms "alkyl", "alkenyl" and "alkoxy" used everywhere in the specification without limitation on chain length or carbon atom number may represent those containing 1–10 carbon atoms, and particularly those containing 1 to 6 carbon atoms, and most preferably those containing 1 to 4 carbon atoms.

The compound of formula (I) according to this invention which is in the form of its amine addition salt may, in general, be less acidic in nature and advantageously less irritant to eyes of mammalian animals, including humans, than the corresponding free carboxylic acid form of the compound of this invention.

The novel cyclohexane derivatives of general formula (I) and their salts according to this invention have useful plant growth regulating activities. Thus, the activities are predominantly of growth retardation, such as stunting or drawfing on the vegetative growth of plants, but various other plant growth regulating effects may be exhibited by varying the nature of plants to be treated and/or the methods, times and rates of application of the compounds. Such plant growth regulating effects which may be induced by the compounds of this invention may include promotion of rooting, reduction in the risk of lodging, promotion of sideshooting and root growth, maintenance of green color of stems and leaves, promotion or delay of flowering, promotion of fruiting and seed ripening, and increase in resistances to temperature hindrance, to phytotoxicity caused by herbicides and to fungal or bacterial diseases. It goes without saying that such a variety of effects as recited above are not always exhibited simultaneously.

According to a second aspect of this invention, therefore, there is provided a plant growth regulating agent comprising as active ingredient at least one of compounds of the formula

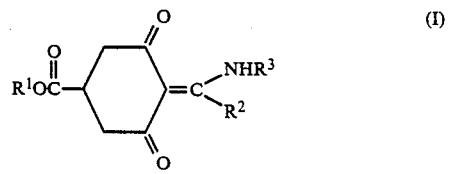

wherein R$^1$ is a hydrogen atom or a lower alkyl group; R$^2$ is a lower alkyl group; R$^3$ is a hydrogen atom, an alkyl group, an alkenyl group, a hydroxyalkyl group, a cycloalkyl group, a morpholino group, an aminoalkyl group, an N-alkylaminoalkyl group, an N,N-dialkylaminoalkyl group, an alkoxycarbonylalkyl group, a group of the formula —(CH$_2$)$_l$—R$^4$ where R$^4$ is a lower alkoxy group, a lower alkylthio group, a benzylthio group, an anilino groups, a morpholino group, a piperazino group, a piperidino group or a lower alkyl-substituted piperidino group and l is 2 or 3, a group of the formula

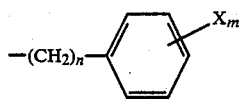

where X is a halogen atom, a lower alkyl group, a lower alkoxy group, a phenoxy group or an alkoxycarbonylalkyloxy group, m is zero or 1 and n is an integer of zero to 2, inclusive, a group of the formula —CH$_2$—R$^5$ is a furyl group, a thenyl group or a pyridyl group, or a group of the formula

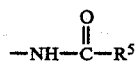

where R$^5$ is as defined above; and a salt of said compounds.

The plant growth regulating agent according to this invention may consist essentially of at least one of the cyclohexane derivatives of general formula (I) and their salts, but more usually and conveniently may be in the form of a composition comprising said active ingredient in combination with a carrier or diluent.

The invention also provides a method of regulating the growth of plant, which comprises applying an effective amount of cyclohexane derivative of formula (I) or a salt thereof, formulated or unformulated, to the foliage or seed of the plant to be treated or to the soil or locus where the plant to be treated is grown.

The active compounds can be applied in a number of ways, for example, they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as slow release granules.

The active compounds are preferably used for agricultural and horticultural purposes in the form of a composition. The type of composition used in any instance will depend upon the particular purpose envisaged. Typical types of composition include wettable powders, granules, grains, emulsions, dusting powders, fine powders, pastes and solutions. Such various types of composition may be formulated in a manner known per se by incorporating appropriate carriers, emulsifiers, dispersants, auxiliaries, and the like.

Typical examples of solid carriers or diluents include talc, bentonite, clay, kaolin, diatomaceous earth, white carbon, vermiculite, slaked lime, calcite, siliceous sand, ammonium sulfate, urea and the like. Typical examples of liquid carriers or diluents include alcohols, dioxane, acetone, methyl ethyl ketone, cyclohexanone, xylene, kerosene, methylnaphthalene, dimethylformamide, dimethylsulfoxide ethylene glycol, and the like. Typical examples of emulsifiers and dispersants include alkyl sulfates, alkyl aryl sulfonates, polyoxyethylene glycol ethers, polyoxyethylene alkyl aryl ethers, polyoxyethylene sorbitan monoalkylates and the like. Typical examples of auxiliaries include carboxymethyl cellulose, arabic gum and the like.

The proportion of the active compound to be formulated into a composition may vary over a wide range depending upon the type of composition and other factors, but typically is 0.5–20% by weight for granules and 5–70% by weight for emulsions or wettable powders, for example.

The plant growth regulating composition according to this invention may be applied, as such or after a further dilution with typically water to form a dilute solution, dispersion or suspension, in an amount effective for the purposes of regulating the growth of plants intended. The rate of application of the active compounds of this invention for the purpose of plant growth regulation will depend on various factors including soil conditions, type of formulation, time and method of application and nature of crop plant or other plant to be treated. In general, however, the rate of application of the active compounds may be in the range of 10 g to 10 Kg per hectare, perferably 40 g to 4 Kg per hectare, especially 100 g to 1 Kg per hectare. Thus, typical rate of application of the active compound for particular purposes will be about 40 g to 160 g per hectare for the purpose of preventing the lodging of aquatic rice plants, about 250 g to 500 g per hectare for preventing the lodging of wheat plants and about 500 g to 4 Kg per hectare for the growth-retardation of lawn grasses.

The plant growth regulating compounds of this invention may be used, if desired, in combination with some other agricultural chemicals and/or fertilizers.

The cyclohexane derivatives of formula (I) and their salts according to this invention, if applied for plant growth regulation purposes to aquatic rice plants and vegetables in their seedling ages, can improve the quality of seedlings particularly in that much better rooting after transplantation and much enhanced resistance to low temperature are achieved. The foliage treatment with those compounds during vegetative ages of crop plants such as aquatic rice, wheat and barley can induce shortening of top leaves and improvement in leaf orientation and thus increase the light utilization efficiency, as a result of which the ripening and overall grain yield of the crop plants can be enhanced. Application of the compounds to stems and foliage of crop plants such as rice, wheat, barley and maize and/or to soil in which the plants are sown, transplanted or grown can control internode elongation and thus prevent or reduce lodging of the plants. Further, the compounds of this invention may suppress useless growth of flowering and garden plants which may be caused by excessively high temperatures and/or insufficient sunshine in green houses.

The plant growth regulating effects of the compounds according to this invention as explained above are very useful not only for agricultural and horticultural treatments but also for control of plant-growth in noncrop lands. For example, the compounds of this invention can be applied to lawn grasses quite advantageously over the known cyclohexane compounds as referred to above in the sense that the stunting or drawfing effect on lawn grasses is substantially stationary, that is with little or no significant variation, over different kinds of these grasses. This is quite noticeable in view of the fact that it is usual or conventional for lawn grasses planted in parks, playing fields, golf links, airports, riverbeds and others to sow a plurality of kinds of grasses in admixture in order to adapt a variety of environmental stresses including diseases, harmful insects, weather and soil conditions. Further, the application of the compounds of this invention to underground grasses in orchard and pastures makes it possible to control or retard the growth or excessive luxuriant growth of plants, to reduce the number of reaping and/or to facilitate the mowing operations as usually required for maintenance. The application of the compounds of this invention to lawn grasses can also promote the emergence of lateral buds and increase the growth density of the grasses.

The following Examples further illustrate, but not limit, this invention. Thus, Examples 1 and 2 illustrate the preparation of the cyclohexane derivatives of formula (I) and an amine salt thereof, Examples 3 to 8 illustrate the preparation of several different forms of the plant growth regulating composition and Examples 9 to 11 illustrate the plant growth regulation effects of typical compounds according to this invention.

EXAMPLE 1

Preparation of Compound 20

A solution of ethyl 3,5-dioxo-4-propionylcyclohexanecarboxylate (2.4 g; 0.01 mol) and aniline (0.9 g; 0.01 mol) in ethyl alcohol (25 ml) was heated under reflux for 2 hours. After the completion of the reaction, the solvent used was distilled off and the resulting crystals were washed with petroleum ether and then recovered by filtration. Recrystallization of the crude crystalline mass from ethyl alcohol gave yellow needles with m.p. 108°–110° C. Yield: 2.0 g (63.4%).

Compounds 1 to 19, 21 to 32, 34 to 72, 75 to 94 and 96 to 100 may also be prepared in a manner similar to that given in Example 1.

EXAMPLE 2

Preparation of Compound 74 (amine salt)

3,5-Dioxo-4-propionylcyclohexanecarboxylic acid (2.0 g; 9.42 mmol) and isopropanolamine (1.42 g; 18.9 mmol) were added to ethyl acetate (25 ml) at room temperature, when crystals were deposited. The crystals were recovered by filtration, washed with ethyl ether and dried to yield the titled compound in the form of a yellow powder with m.p. 140°–143° C. Yield: 2.8 g (87.3%).

Compounds 33, 73, 74 and 101 to 108 may also be prepared in the same way as that given in Example 2.

EXAMPLE 3

Preparation of Compound 95 (oxalic acid salt)

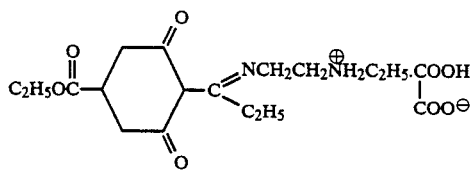

A solution of oxalic acid (0.38 g; 4.2 mmol) in ethanol (25 ml) was added to a solution of ethyl 4-[1-(2-ethylamino-ethylamino)propylidene]-3,5-dioxocyclohexane carboxylate (1.3 g; 4.2 mmol) in chloroform (25 ml) at room temperature whereby to deposit crystals. The crystals were recovered by filtration, washed with ethyl ether and dried to afford the titled compound in the form of white powder with m.p. 182°–184° C. Yield: 1.2 g (71.4%).

EXAMPLE 4

Wettable powder

A composition in the form of a wettable powder was prepared by homogeneously mixing and pulverizing, on the weight basis, 10% of Compound 1, 85% of diatomaceous earth, 2% of disodium di-naphthylmethane disulfonate and 3% of sodium lignosulfonate.

EXAMPLE 5

Emulsifiable concentrate

An emulsifiable concentrate was made up by mixing the ingredients undermentioned and stirring the mixture until all the constituents were dissolved.

| | |
|---|---|
| Compound 8 | 30% by weight |
| Cyclohexanone | 20% by weight |
| Polyoxyethylene alkyl aryl ether | 11% by weight |
| Calcium alkylbenzenesulfonate | 4% by weight |
| Methyl naphthalene | 35% by weight |

EXAMPLE 6

Granules

A composition in the form of granules was prepared by homogeneously mixing and pulverizing together, on the weight basis, 5% of Compound 21, 2% of sodium lauryl sulfate, 5% of sodium lignosulfonate, 2% of carboxymethyl cellulose, 30% of bentonite and 56% of clay, followed by adding 20% of water per 80% of the pulverized mixture. The resulting mixture was kneaded and granulated on an extruder in the form of granules of 14–32 mesh size and finally dried.

EXAMPLE 7

Dusting powder

On the weight basis, 4% of Compound 31, 5% of white carbon and 91% of clay were homogeneously mixed and pulverized to give a dusting powder.

EXAMPLE 8

Paste

A composition in the form of a paste was prepared by homogeneously mixing together, on the weight basis, 5% of Compound 15, 1% of xylene, 5% of polyoxyethylene sorbitan monolaurate and 89% of white vaseline.

EXAMPLE 9

Solution

A composition in the form of a solution was prepared by dissolving, on the weight basis, in 65% of water, 20% of Compound 74, 5% of polyoxyethylene alkyl aryl ether and 10% of polyoxyethylene alkylamine.

EXAMPLE 10

Growth retardation test on aquatic rice seedlings

The compounds of this invention as shown in Table 2 below each in the form of a wettable powder as prepared in Example 4 above and "chlormequat" as reference compound which was also prepared in the form of a corresponding wettable powder each were diluted with a volume of water such that 1000 liters of the aqueous composition so prepared were applied per hectare with an application rate of the active compound being 1 Kg/hectare. Each composition thus prepared was applied to the stem and foliage of each seedling of an aquatic rice (form: Kinmaze) at the growth period with fully expanded second true leaf.

After each of the seedlings so treated had grown to have the fifth true leaf fully extracted, assessment was made by measuring the height of up to the apex of the fifth leaf of each seedling for ten seedlings per plot and evaluating the stunting effect as a percentage retardation of the average growth of seedlings in respect of the growth of the untreated control. The results are shown in Table 2, where the numerals of the percentage retardation are given as integers by counting fractions of 0.5 and over as a whole number and disregarding the rest.

TABLE 2

| Compound No. tested | Percentage growth retardation(%) | Compound No. tested | Percentage growth retardation(%) |
| --- | --- | --- | --- |
| 1 | 30 | 18 | 51 |
| 2 | 23 | 19 | 34 |
| 3 | 60 | 20 | 58 |
| 4 | 52 | 21 | 45 |
| 5 | 32 | 22 | 26 |
| 6 | 57 | 23 | 15 |
| 7 | 57 | 24 | 49 |
| 8 | 60 | 25 | 49 |
| 9 | 63 | 26 | 51 |
| 10 | 66 | 27 | 53 |
| 11 | 60 | 28 | 51 |
| 12 | 53 | 29 | 44 |
| 13 | 58 | 30 | 38 |
| 14 | 68 | 31 | 59 |
| 15 | 56 | 32 | 62 |
| 16 | 43 | 33 | 60 |
| 17 | 35 | chlormequat (comparative) | 6 |

EXAMPLE 11

Stunting test on a variety of lawn grasses

Seeds of four kinds of lawn grasses, i.e. Kentucky bluegrass, Creeping redfescue, Pencross bentgrass and perennial ryegrass, were sown in biscuit pots (diameter: 15 cm) and grown up therein. Then, the growing seedlings of these grasses were trimmed to 1-2 cm in height and several compounds of this invention and a reference compound shown in Table 3 below were applied to the stems and leaves of the grasses. Each of the compounds to be tested being formulated in the form of a wettable powder as shown in Example 4 was used as an aqueous diluted composition prepared by diluting it with a volume of water such that 1000 liters of the aqueous composition so prepared were applied per hectare with a rate of application of the active compound being 1 Kg/hectare.

Three weeks after the treatment with the compounds, the height of grasses tested was measured and the percentage growth retardation was evaluated for each test grass in respect of the growth of the untreated control which gave the height of grass of 11-13 cm.

The results are shown in Table 3, where the numerals of percentage growth retardation are given as integers by counting fractions of 0.5 and over as a whole number and disregarding the rest.

TABLE 3

| Compound No. tested | Kentucky bluegrass | Creeping redfescue | Pencross bentgrass | Perennial ryegrass |
| --- | --- | --- | --- | --- |
| 3 | 50 | 55 | 53 | 50 |
| 7 | 56 | 47 | 53 | 48 |
| 11 | 55 | 53 | 55 | 52 |
| 14 | 57 | 54 | 56 | 55 |
| 20 | 52 | 47 | 49 | 54 |
| 31 | 54 | 51 | 55 | 52 |
| Reference | 41 | 26 | 57 | 15 |

TABLE 3-continued

| Compound No. tested | Kentucky bluegrass | Creeping redfescue | Pencross bentgrass | Perennial ryegrass |
| --- | --- | --- | --- | --- |
| compound | | | | |

Note
Reference compound used in this Example is 5-ethoxy-carbonyl-2-propionylcyclohexane-1,3-dione which is described in Japanese Patent Application Kokai No. 164543/83.

The results of Table 3 show that the compounds according to this invention are superior to the reference compound in effect such that the growth of lawn grasses, i.e. the extension of the length of lawn grasses, can be retarded much more uniformly. This implies that the compounds of this invention are particularly useful for lightening the trimming works of lawn grasses in mixed sowing and growing system for a plurality of kinds of lawn grasses generally adopted in cold northern areas, etc.

EXAMPLE 12

Growth retardation test on aquatic rice seedlings

Aquatic rice seedlings with fully expanded second true leaf (form: Kin-maze) were sprayed over their stems and leaves with each of aqueous dilute compositions of the compounds of this invention and a reference compound "chlormequat" as shown in Table 4 below. The aqueous dilute compositions each were prepared from a wettable powder as shown in Example 4 by dilution with a volume of water such that 1000 liters of the aqueous composition so prepared were applied per hectare with a rate of application of the active compound being 1 Kg/hectare.

After each of the seedlings so treated had grown to have the fifth true leaf fully extracted, assessment was made by measuring the height of up to the apex of the fifth leaf of each seedling for ten seedlings per plot and evaluating the stunting effect as a percentage growth retardation of seedlings in respect of the growth of the untreated control. The results are shown in Table 4, where the numerals of the percentage retardation are given as integers by counting fractions of 0.5 and over as a whole number and disregarding the rest.

TABLE 4

| Compound No. tested | Percentage growth retardation (%) | Compound No. tested | Percentage growth retardation (%) |
| --- | --- | --- | --- |
| 34 | 57 | 58 | 55 |
| 35 | 41 | 59 | 49 |
| 36 | 53 | 62 | 47 |
| 37 | 46 | 63 | 42 |
| 38 | 51 | 67 | 30 |
| 39 | 50 | 72 | 48 |
| 41 | 58 | 73 | 45 |
| 42 | 52 | 74 | 58 |
| 43 | 48 | 75 | 61 |
| 44 | 41 | 76 | 52 |
| 45 | 58 | 77 | 50 |
| 46 | 59 | 79 | 43 |
| 47 | 61 | 80 | 36 |
| 48 | 49 | 81 | 59 |
| 49 | 54 | 82 | 44 |
| 50 | 60 | 83 | 40 |
| 51 | 46 | 84 | 26 |
| 52 | 54 | 85 | 32 |
| 53 | 45 | 86 | 29 |
| 55 | 48 | 87 | 49 |
| 56 | 60 | 88 | 45 |
| 57 | 59 | 89 | 56 |
| 90 | 63 | 100 | 60 |
| 91 | 67 | 101 | 53 |
| 92 | 49 | 102 | 54 |

TABLE 4-continued

| Compound No. tested | Percentage growth retardation (%) | Compound No. tested | Percentage growth retardation (%) |
|---|---|---|---|
| 93 | 66 | 103 | 50 |
| 94 | 63 | 104 | 48 |
| 95 | 56 | 105 | 51 |
| 96 | 52 | 106 | 46 |
| 97 | 58 | 107 | 57 |
| 98 | 55 | 108 | 53 |
| 99 | 61 | chlormequat | 3 |

EXAMPLE 13

Growth retardation test on aquatic rice seedlings

The procedure of Example 12 above was repeated except that the rate of application of active compound was 0.125 Kg/hectare. Compound numbers tested in this Example and the results obtained are shown in Table 5 below. The assessment was also made in the same way as in Example 12.

TABLE 5

| Compound No tested | Percentage growth retardation (%) |
|---|---|
| 34 | 32 |
| 39 | 28 |
| 43 | 26 |
| 47 | 41 |
| 74 | 42 |
| 76 | 29 |
| 77 | 31 |
| 89 | 35 |
| 90 | 48 |
| 97 | 35 |
| 94 | 37 |
| 107 | 34 |

What we claim is:

1. A compound of formula (I)

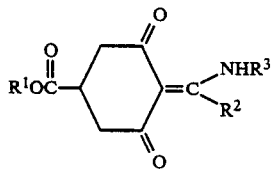

wherein $R^1$ is a hydrogen atom or a lower alkyl group; $R^2$ is a lower alkyl group; $R^3$ is a hydrogen atom, an alkyl group of 1-6 carbon atoms, an alkenyl group of 1-6 carbon atoms, a hydroxyalkyl group of 1-6 carbon atoms, a cycloalkyl group of 3-6 carbon atoms, an aminoalkyl group of 1-6 carbon atoms, an N-alkylaminoalkyl group of 1-6 carbon atoms, an N,N-di-alkylaminoalkyl group of 1-6 carbon atoms, an alkoxycarbonylalkyl group of 1-6 carbon atoms, a group of the formula $-(CH_2)_l-R^4$ where $R^4$ is a lower alkoxy group, a lower alkylthio group, a benzylthio group, an anilino group, l is 2 or 3, a group of the formula

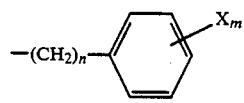

where X is a halogen atom, a lower alkyl group, a lower alkoxy group, a phenoxy group or an alkoxycarbonylalkyloxy group of 1-6 carbon atoms, m is zero or 1 and n is an integer of zero to 2, inclusive, a group of the formula $-CH_2-R^5$ where $R^5$ is a group of the formula

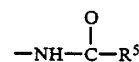

where $R^5$ is as defined above; and a salt of said compound.

2. A compound of claim 1 which is a compound of formula (I) where $R^1$ is a hydrogen atom or a lower alkyl group; $R^2$ is a lower alkyl group; and $R^3$ is a lower alkyl group, a hydroxyalkyl group, an N-alkylaminoalkyl group, an N,N-dialkylaminoalkyl group, an alkoxycarbonylalkyl group, or a group of the formula

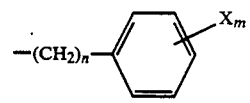

where X is a halogen atom, a lower alkyl group, a lower alkoxy group or a phenoxy group, m is zero or 1 and n is zero or 1; and an amine-addition salt of said compound.

3. A compound of Claim 1 which is a compound of formula (I) wherein $R^1$ is a hydrogen atom or a lower alkyl group; $R^2$ is a lower alkyl group; and $R^3$ is a hydrogen atom, an alkenyl group of 1-10 carbon atoms, a cycloalkyl group of 3-6 carbon atoms, an aminoalkyl group, a group of the formula $-(CH_2)_l-R^4$ where $R^4$ is a lower alkoxy group, a lower alkylthio group, a benzylthio group, an anilino group, and l is an integer of 2 or 3, a group of the formula

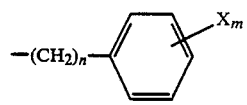

where X is an alkoxycarbonylalkyloxy group of 1-10 carbon atoms, m is zero or 1 and n is an integer of zero to 2; and an amine-addition salt of said compound.

4. A compound of claim 1 which is a compound of formula (I) where $R^1$ is a hydrogen atom or a lower alkyl group; $R^2$ is a lower alkyl group; and $R^3$ is a lower alkyl group; and an amine-addition salt of said compound.

5. A compound of claim 1 which is a compound of formula (I) where $R^1$ is a hydrogen atom or a lower alkyl group; $R^2$ is a lower alkyl group; and $R^3$ is a hydroxyalkyl group of 1-10 carbon atoms; and an amine-addition salt of said compound.

6. A compound of claim 1 which is a compound of formula (I) where $R^1$ is a hydrogen atom or a lower alkyl group; $R^2$ is a lower alkyl group; and $R^3$ is an N-alkylaminoalkyl group of 1-10 carbon atoms or an N,N-di-alkylaminoalkyl group of 1-10 carbon atoms; and an amine-addition salt of said compound.

7. A compound of claim 1 which is a compound of formula (I) where $R^1$ is a lower alkyl group; $R^2$ is a lower alkyl group; and $R^3$ is an alkoxycarbonylalkyl group of 1-10 carbon atoms; and an amine-addition salt of said compound.

8. A compound of claim 1 which is a compound of formula (I) where $R^1$ is a hydrogen atom or a lower alkyl group; $R^2$ is a lower alkyl group; and $R^3$ is a phenyl group optionally bearing a halogen atom, an alkyl group, an alkoxy group of 1–10 carbon atoms or a phenoxy group as the substituent on the phenyl group.

9. A compound of claim 1 which is a compound of formula (I) where $R^1$ is a hydrogen atom or a lower alkyl group; $R^2$ is a lower alkyl group; and $R^3$ is a group of the formula

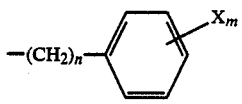

where X is a halogen atom, an alkyl group of 1–10 carbon atoms, an alkoxy group of 1–10 carbon atoms, or a phenoxy group, m is zero or 1 and n is 1 or 2; and an amine-addition salt of said compound.

10. A compound of claim 1 which is a compound of formula (I) where $R^1$ is a hydrogen atom or a lower alkyl group; $R^2$ is a lower alkyl group; and $R^3$ is a group of the formula $-(CH_2)_l R^4$ where $R^4$ is an alkoxy group of 1–10 carbon atoms, l is 2 or 3; and an amine-addition salt of said compound.

11. A compound of claim 1 which is a compound of formula (I) where $R^1$ is a hydrogen atom or a lower alkyl group; $R^2$ is a lower alkyl group; and $R^3$ is a group of the formula $-(CH_2)_l-R^4$ where $R^4$ is an alkylthio group or a benzylthio group, and l is 2 or 3; and an amine-addition salt of said compound.

12. A compound of claim 1 which is an amine-addition salt of the compound of formula (I) where $R^1$ is a hydrogen atom, with an amine of the formula $R^{3'}-NH_2$ where $R^{3'}$ has the same meaning as $R^3$ except excluding a group of the formula

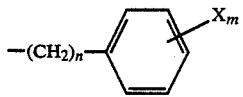

where n=0, preferably $R^{3'}$ being hydroxy(lower)alkyl, said amine being added to the carboxyl group of the compound of formula (I) where $R^1$ is the hydrogen atom.

13. A compound of claim 1 which is an amine-addition salt of the compound of formula (I) where $R^1$ is a hydrogen atom, with an amine of the formula $R^{3'}-NH_2$ where $R^{3'}$ is a hydroxy(lower)alkyl group, a (lower)alkyl group, a di-(lower)alkylamino(lower)alkyl group, a (lower)alkoxycarbonyl(lower)alkyl group, or a (lower)alkoxy(lower)alkyl group, said amine being added to the carboxyl group of the compound of formula (I) where $R^1$ is the hydrogen atom.

14. A compound of claim 1 which is selected from 4-[1-(2-hydroxyethylamino)propylidene]-3,5-dioxocyclohexane-carboxylic acid and 2-hydroxyethylamine salt thereof.

15. A compound of claim 1 which is ethyl 4-(1-phenylaminopropylidene)-3,5-dioxocyclohexanecaboxylate.

16. A compound of claim 1 which is selected from ethyl 4-[1-(3-hydroxypropylamino)propylidene]-3,5-dioxocyclohexane-carboxylate (Compound No. 39); 4-[1-(2-hydroxypropylamino)propylidene]-3,5-dioxocyclohexane-carboxylic acid; and 4-[1-(2-hydroxypropylamino)propylidene]-3,5-dioxocyclohexane-carboxylic acid 2-hydroxypropylamine salt.

17. A compound of claim 1 which is selected from ethyl 4-[1-(2-methoxyethylamino)propylidene]-3,5-dioxocyclohexane-carboxylate (Compound No. 76); and ethyl 4-[1-(3-methoxypropylamino)propylidene]-3,5-dioxocyclohexane-carboxylate.

18. A compound of claim 1 which is ethyl 4-[1-(2-methylthio-ethylamino)propylidene]-3,5-dioxocyclohexane-carboxylate.

19. A plant growth regulating composition comprising as the active ingredient at least one of a compound of the formula

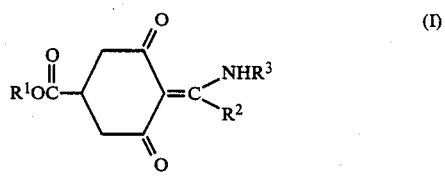

wherein $R^1$ is a hydrogen atom or a lower alkyl group; $R^2$ is a lower alkyl group; $R^3$ is a hydrogen atom, an alkyl group of 1–6 carbon atoms, an alkenyl group of 1–6 carbon atoms, a hydroxyalkyl group of 1–6 carbon atoms, a cycloalkyl group of 3–6 carbon atoms, an aminoalkyl group of 1–6 carbon atoms, an N-alkylaminoalkyl group of 1–6 carbon atoms, an N,N-di-alkylaminoalkyl group of 1–6 carbon atoms, an alkoxycarbonylalkyl group of 1–6 carbon atoms, a group of the formula $-(CH_2)_l-R^4$ where $R^4$ is a lower alkoxy group, a lower alkylthio group, a benzylthio group, an anilino group, and l is 2 or 3, a group of the formula

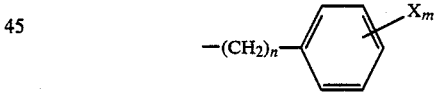

where X is a halogen atom, a lower alkyl group, a lower alkoxy group, a phenoxy group or an alkoxycarbonylalkyloxy group of 1–6 carbon atoms, m is zero or 1 and n is an integer of zero to 2, inclusive, a group of the formula $-CH_2-R^5$ where $R^5$ is a group of the formula

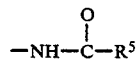

where $R^5$ is as defined above; and a salt of said compound in an amount effective to regulate growth of plants, in association with a solid or liquid carrier for the active ingredient.

* * * * *